(12) United States Patent
Dummer et al.

(10) Patent No.: US 6,990,848 B2
(45) Date of Patent: Jan. 31, 2006

(54) SYSTEM AND METHOD FOR DETERMINING MATERIAL PROPERTIES OF SAMPLES

(75) Inventors: Andrew Kirk Dummer, Durham, NC (US); Robert Ernest Troxler, Raleigh, NC (US); Michael Eric Bienvenu, Cary, NC (US)

(73) Assignee: Trxoler Electronic Laboratories, Inc., Research Triangle Park, NC (US)

(*) Notice: Subject to any disclaimer, the term of this patent is extended or adjusted under 35 U.S.C. 154(b) by 131 days.

(21) Appl. No.: 10/632,034

(22) Filed: Jul. 30, 2003

(65) Prior Publication Data

US 2004/0098217 A1     May 20, 2004

Related U.S. Application Data

(60) Provisional application No. 60/401,186, filed on Aug. 5, 2002.

(51) Int. Cl.
   *G01N 15/08*     (2006.01)
(52) U.S. Cl. ............................... 73/38; 73/433
(58) Field of Classification Search .................. 73/861, 73/219, 220, 861.42, 861.46, 38, 433; 702/50
   See application file for complete search history.

(56) References Cited

U.S. PATENT DOCUMENTS

| | | |
|---|---|---|
| 4,083,228 A | 4/1978 | Turner et al. |
| 4,095,473 A | 6/1978 | Batchelor et al. |
| 4,112,738 A | 9/1978 | Turner |
| 4,154,098 A | 5/1979 | Pelletier |
| 4,184,371 A | 1/1980 | Brachet |
| 5,022,261 A | 6/1991 | Wolfson et al. |
| 5,074,146 A | 12/1991 | Orr et al. |
| 5,608,157 A | 3/1997 | Orr et al. |
| 5,637,810 A | 6/1997 | Conner, Jr. |
| 5,744,699 A | 4/1998 | Suzuki |
| 5,760,293 A | 6/1998 | Orr et al. |
| 6,082,174 A | 7/2000 | Lee et al. |

FOREIGN PATENT DOCUMENTS

| | | |
|---|---|---|
| EP | 0 501 811 A1 | 9/1992 |
| EP | 0 689 044 A1 | 12/1995 |

*Primary Examiner*—John E. Chapman
*Assistant Examiner*—Rodney Frank
(74) *Attorney, Agent, or Firm*—Alston & Bird LLP (57) ABSTRACT

A method is provided for nondestructively determining a material property of a porous sample. A first vessel is evacuated to a sub-atmospheric pressure, while a test pressure, greater than the sub-atmospheric pressure, is established in a second vessel containing the sample. The pressures of the first and second vessels are equalized by opening a valve mechanism therebetween. The resulting pressure change in the second vessel exhibits an initial pressure drop followed by a transition to an equalization pressure. The envelope volume of the sample is determined from a minimum pressure attained by the second vessel upon initial opening of the valve mechanism, wherein the minimum pressure is related to the initial pressure drop. The envelope density of the sample is thus a quotient of the mass and the envelope volume of the sample. The absolute density and relative absorption of the sample may also be determined and an associated system is provided.

20 Claims, 3 Drawing Sheets

SYSTEM AND METHOD FOR DETERMINING MATERIAL PROPERTIES OF SAMPLES

CROSS-REFERENCE TO RELATED APPLICATIONS

This application claims priority to U.S. Provisional Patent Application Ser. No. 60/401,186, filed Aug. 5, 2002, which is hereby incorporated herein in its entirety by reference.

BACKGROUND OF THE INVENTION

1. Field of the Invention

The present invention relates to a system and method for determining material properties and, more particularly, to a system and method for the determining the specific gravity, the density, and the absorption of uncompacted bituminous paving mixtures, as well as the bulk and absolute specific gravities and absorption properties of soils and aggregates, and the bulk specific gravity, permeability, and porosity of field cores and laboratory prepared specimens of compacted bituminous material.

2. Description of Related Art

In the construction industry, knowledge of the physical characteristics of the materials to be used during various phases of the construction process is often required. Among these materials, for example, are soils, aggregates and bituminous paving mixtures. The absolute (apparent), maximum, and bulk densities (or specific gravities) of these materials, as well as the absorption thereof, generally comprise material characteristics of common interest. The determination of these values for both coarse and fine aggregates can be time consuming, since the measurement procedure often requires the test sample to be soaked in a water bath for a period of 24 hours. Such measurement methods and procedures can be found in, for example, ASTM Standard Nos. C128-97, *Standard Test Method for Specific Gravity and Absorption of Fine Aggregate* and C127-88, *Standard Test Method for Specific Gravity and Absorption of Coarse Aggregate*, which are incorporated herein by reference.

The standard method for determining the theoretical maximum specific gravity and density of bituminous paving mixtures, also referred to herein as the "Rice method" and the result of which is referred to herein as the "Rice value", involves the use of a system comprising a water-filled pycnometer operating in conjunction with a vacuum pump and associated lines, and a mass balance. The details of this method can be found in ASTM Standard No. D2041-00, *Standard Test Method for Theoretical Maximum Specific Gravity and Density of Bituminous Paving Mixtures*, which is also incorporated herein by reference. In asphalt paving, the Rice value for a bituminous paving mixture is commonly used as the benchmark against which the density of field compacted material is compared. However, the Rice method may be cumbersome, time-consuming, subject to inaccuracies, and destructive with respect to the sample since the necessary measurements are conducted with the sample immersed in water.

Thus, there exists a need for a system and method capable of nondestructively determining the specific gravity, absorption, and other properties of soils, aggregates, and bituminous paving mixtures. Such a system and method should desirably be capable of expeditiously producing the analysis of the sample, with minimal handling thereof, to obtain the necessary results with improved precision over commonly used methods.

BRIEF SUMMARY OF THE INVENTION

The above and other needs are met by the present invention which, in one embodiment, provides a method for nondestructively determining a material property of a porous sample. A first vessel is evacuated to a sub-atmospheric pressure, while a test pressure is established in a second vessel having the sample disposed therein, and wherein the test pressure is greater than the sub-atmospheric pressure. The pressures of the first and second vessels are then equalized by opening a valve mechanism operably engaged between the first and second vessels. Each of the first and second vessels thereby experience a pressure change, wherein the pressure change in the second vessel exhibits an initial pressure drop followed by a transition to an equalization pressure on a pressure vs. time curve. The envelope volume of the sample is then determined from a minimum pressure attained by the second vessel upon initial opening of the valve mechanism, wherein the minimum pressure is related to the initial pressure drop. The envelope density of the sample is then determined as a quotient of the mass and the envelope volume of the sample.

Another advantageous aspect of the present invention comprises a system for nondestructively determining a property of a porous sample having a mass. Such a system includes a first vessel capable of being evacuated to a sub-atmospheric pressure and a second vessel having the sample disposed therein and capable of being established at a test pressure, wherein the test pressure is greater than the sub-atmospheric pressure. A valve mechanism is operably engaged between the first and second vessels and is configured such that opening of the valve mechanism allows the pressures of the first and second vessels to equalize to an equalization pressure. A monitoring device is configured to determine a pressure change in the second vessel when the valve mechanism is opened, wherein the pressure change is indicative of a minimum pressure attained by the second vessel upon initial opening of the valve mechanism. The minimum pressure is related to an envelope volume of the sample, and thus a quotient of the mass and the envelope volume of the sample thereby provides an envelope density of the sample.

Thus, embodiments of the present invention provide a system and method capable of nondestructively determining the specific gravity, absorption, and other properties of soils, aggregates, and bituminous paving mixtures by utilizing the displacement of a gas in order to determine the volume of the sample. In addition, embodiments of the present invention provide a system and method capable of expeditiously producing the analysis of the sample, with minimal handling thereof, to obtain the necessary results with improved precision over commonly used methods. As such, embodiments of the present invention reduce the time necessary to perform the necessary sample analysis, while providing a higher degree of repeatability without contaminating or destroying the sample, thereby making the sample available for subsequent testing. Accordingly, embodiments of the present invention provide significant advantages as detailed herein.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
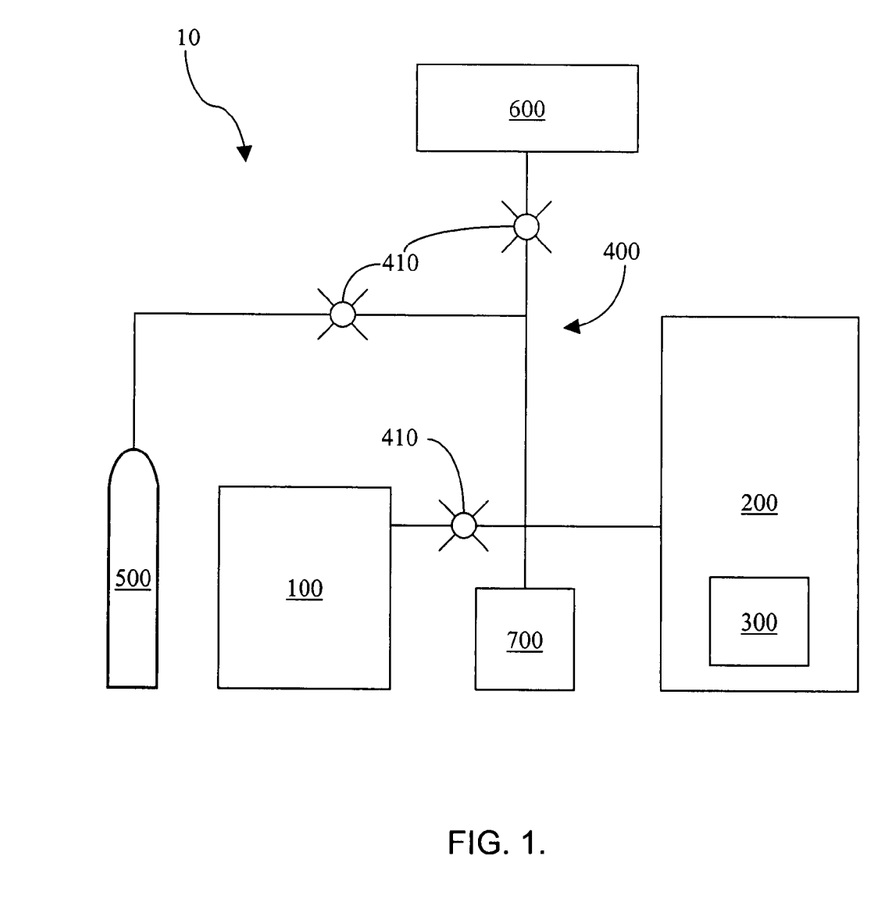
FIG. 1 is a schematic of a system for nondestructively determining a material property of a sample according to one embodiment of the present invention.

FIG. 1 illustrates a system for nondestructively determining a property of a sample according to one embodiment of the present invention, the system being indicated generally by the numeral 10. Such a system 10 comprises a first vessel 100, a second vessel 200 configured to receive a sample 300 therein, a valve mechanism 400 in communication between the first vessel 100 and second vessel 200, a gas source 500 and a vacuum source 600 both in communication with the valve mechanism 400, and a monitoring device 700. According to one advantageous aspect of the present invention, the system 10 is configured to determine the volume of, for example, a soil, aggregate, or bituminous paving mixture sample 300 and, in turn, the density and specific gravity thereof so as to provide the necessary data required by applicable standards such as, for instance, ASTM Standard D2041, as previously mentioned.

More particularly, embodiments of the present invention utilize the ideal gas law of thermodynamics (PV=nRT) to determine the volume of a sample 300, where P is the pressure, V is the volume, n is the number of moles of gas, R is a constant, and T is the temperature in degrees Kelvin. Determination of the volume of the sample 300 is accomplished by measuring the change in pressure as a gas is expanded from a closed second vessel 200 with a known volume, having the sample 300 disposed therein and established at a test pressure, into an evacuated first vessel 100 also having a known volume. As shown in FIG. 1, in order to accomplish the determination of the volume of the sample 300 (also referred to herein as "$V_s$"), the first and second vessels 100, 200 are sealable (and also referred to herein as "$V_1$" and "$V_2$", respectively), wherein the vessels 100, 200 may also be operably engaged with a device for monitoring the pressure therein such as, for example, a monitoring device 700 associated with the valve mechanism 400, or a pressure gauge operably engaged with each vessel 100, 200. The first and second vessels 100, 200, in one embodiment, are comprised of aluminum due to, for example, thermodynamic considerations, as will be appreciated by one skilled in the art from the description herein of the applied methodology of the present invention. The gas source 500 is configured to provide a substantially inert gas such as, for example, helium, nitrogen, or carbon dioxide, while the vacuum source 600 comprises, for example, a vacuum pump. The gas source 500, vacuum source 600, and vessels 100, 200 are interconnected with appropriate tubing to one or more valves 410 comprising the valve mechanism 400. The vessels 100, 200 are further optimized for expanding the gas from the second vessel 200 containing the sample 300, as will be appreciated by one skilled in the art and as discussed further herein with regard to a propagation of error analysis for a system 10 as described.

Prior to the analysis of the sample 300, the system 10 is first calibrated by, for example, performing a series of measurements, first with both vessels empty and then with a calibration object of known volume disposed within the second vessel 200. The volumes $V_1$ and $V_2$ are then found, for a system configuration in which the sample 300 is placed in $V_2$ and the gas is expanded from $V_2$ into $V_1$, so as to obtain an equalization pressure $P_c$, as follows:

$$V_1 = V_c \frac{(P_c P_o - P_o^2 - P_e P_c + P_e P_o)}{(P_e P_v - P_e P_o - P_c P_o + P_v P_c)}$$

$$V_2 = V_c \frac{(P_v P_o - P_e P_o - P_v P_c + P_e P_c)}{(P_e P_v - P_e P_o - P_c P_o + P_v P_c)}$$

$V_c$ ≡ volume of calibration object
$P_v$ ≡ evacuated pressure in $V_1$ prior to expansion
$P_o$ ≡ pressure in $V_2$ prior to expansion
$P_e$ ≡ expanded pressure in $V_1$ without calibration object
$P_c$ ≡ expanded pressure in $V_1$ with calibration object Thereafter, in order to measure the unknown volume $V_s$ of a sample 300, the sample 300 is placed in $V_2$ and the gas is expanded into $V_1$ so as to attain the equalization pressure $P_s$. The volume $V_s$ of the sample 300 is then determined according to the following relationship:

$$V_s = \frac{P_v V_1 + P_o V_2 - P_s(V_1 + V_2)}{P_o - P_s}$$

One skilled in the art will appreciate that the system 10 must be properly prepared prior to implementing the methods as detailed herein. For example, the system 10 may be first evacuated using the vacuum source 600 acting upon the two vessels 100, 200 and the valve mechanism 400 via a connection to the valve mechanism 400. Such a procedure removes or purges air from the system 10 as well as any water that may be present in the system 10 or the sample 300. The application of the vacuum also causes the vaporization of any water in the sample 300, which facilitates removal of the water from the sample 300. The vessels 100, 200 and the valve mechanism 400 may then be backfilled with the gas from the gas source 500 via a connection to the valve mechanism 400. Such a vacuum and backfill procedure may be repeated as necessary, and monitored by the monitoring device 700, in order to ensure that the vessels 100, 200 and valve mechanism 400, as well as the pores of the sample 300, are essentially filled only with the gas. Upon completion of this purging process, the methods as described herein are accomplished in accordance with the presented underlying theories.

Embodiments of the present invention are particularly directed to determining the volume of a sample 300 using two vessels 100, 200 and a gas displacement methodology according to the Ideal Gas Law. However, by this technique, there are two possible methods by which the volume of the sample 300 can be determined. As shown in FIG. 1, a sample 300 having an unknown volume is placed in the second vessel 200. As such, one method of determining the volume of the sample 300 is to evacuate the second vessel 200 and pressurize the first vessel 100, whereafter the vessels 100, 200 are connected and the pressure allowed to equilibrate therebetween. A second method for determining the volume of the sample 300 is to evacuate the first vessel 100 and then pressurize the second vessel 200, before equilibrating the pressure between the two vessels 100, 200. The evacuated vessel may be evacuated to a pressure of, for example, about 20 Torr, while the pressurized vessel may be established at a pressure of, for example, about 700 Torr.

In comparing the two methods of determining the volume of the sample 300, a propagation of error analysis was performed in order to determine which method provided the result with the highest precision. For each method, the equation for $V_s$ was determined as a function of $P_o$ (the positive pressure established in either the first vessel 100 or the second vessel 200 prior to equilibration), $P_s$ (the pressure following equilibration), the volume $V_1$ of the first vessel 100, and the volume $V_2$ of the second vessel 200. Thereafter, the partial derivatives with respect to each of the independent variables were determined, multiplied by the respective uncertainty ($s_x$), and then added in quadrature. As will be appreciated by one skilled in the art, the result of the propagation of error analysis thereby provides an estimate of the total uncertainty in the measurement method as a function of $V_1$ and $V_2$ and $V_s$. The following are the partial derivatives as well as the equation for the total uncertainty.

Propagation of Error for Expanding from $V_1$ to $V_2$ $$Po \cdot V1 = Ps \cdot (V1 + V2 - Vs)$$

$$Vs = V1 + V2 - \frac{Po}{Ps} \cdot V1$$

$$\frac{d}{dPo}\left(V1 + V2 - \frac{Po}{Ps} \cdot V1\right)$$

$$\frac{d}{dPo}Vs = \frac{-1}{Ps} \cdot V1$$

$$\frac{d}{dPs}Vs = \frac{Po}{Ps^2} \cdot V1$$

$$\frac{d}{dV1}Vs = \frac{-(Po-Ps)}{Ps}$$

$$\frac{d}{dV2}Vs = 1$$

Propagation of Error for Expanding from $V_2$ to $V_1$ $$Po \cdot (V2 - Vs) = Ps \cdot (V1 + V2 - Vs)$$

$$Vs = V2 - \frac{1}{(Po-Ps)} \cdot Ps \cdot V1$$

$$\frac{d}{dPs}Vs = V1 \cdot \frac{Po}{(Po-Ps)^2}$$

$$\frac{d}{dPo}Vs = \frac{1}{(Po-Ps)^2} \cdot Ps \cdot V1$$

$$\frac{d}{dV1}Vs = \frac{-1}{(Po-Ps)} \cdot Ps$$

$$\frac{d}{dV2}Vs = 1$$

$$s_{Vs} = \sqrt{\left(\frac{d}{dPo}Vs\right)^2 \cdot (s_{Po})^2 + \left(\frac{d}{dPs}Vs\right)^2 \cdot (s_{Ps})^2 + \left(\frac{d}{dV1}Vs\right)^2 \cdot (s_{V1})^2 + \left(\frac{d}{dV2}Vs\right)^2 \cdot (s_{V2})^2}$$

A numerical minimization can then be performed for each of these cases resulting in an optimal ratio for the volumes $V_1$ and $V_2$ and a minimum uncertainty in the measured quantity. The results of this analysis indicated that the second method (expanding from $V_2$ to $V_1$) was slightly more precise having an uncertainty which was 5–10% smaller than that of the first method, depending on the size of the sample 300. Further, in one embodiment, an advantageous ratio of volumes $V_1$ and $V_2$ was found to be about 2:5.

The mass of the sample 300 is also determined such that, as a result, the density of the sample 300 may be obtained by dividing the mass of the sample 300 by the volume $V_s$ thereof. The density of the sample 300 may thus be expressed in units of, for example, g/cm$^3$, while the specific gravity of the sample 300 is determined as the unitless ratio of the mass or density of the sample 300 to the mass or density, respectively, of an equal volume of water, both at the same temperature such as, for example, 25° C.

To obtain data with sufficient precision using a method and apparatus according to the present invention, an appropriate sample size should be used. For example, in the case of a bituminous paving material, the following sample size guidelines would be recommended:

| Size of Largest Particle of Aggregate in Mixture, mm (in.) | Minimum Sample Size, g |
|---|---|
| 50.0 (2) | 6000 |
| 37.5 (1½) | 4000 |
| 25.0 (1) | 3000 |
| 19.0 (¾) | 2000 |
| 12.5 (½) | 1500 |

-continued

| Size of Largest Particle of Aggregate in Mixture, mm (in.) | Minimum Sample Size, g |
|---|---|
| 9.5 (3/8) | 1500 |
| 4.75 (No. 4) | 1500 |

In some instances, the capacity of the second vessel 200 may be limited. For example, in one embodiment, the second vessel 200 may have a volume $V_2$ of 2000 cm$^3$. In such instances, if the sample 300 has a mass greater than 2000 g, the sample 300 may be divided into two or more portions. Further, where the sample 300 has a mass of 6000 g, the sample 300 should be divided into three portions, each portion having a mass of 2000 g. In other instances, according to some embodiments of the present invention, a sample 300 should preferably have a mass of at least 1500 g.

A result of the described procedure is a density that is indicative of the absolute or apparent specific gravity (Gsa) of the sample 300, as will be appreciated by one skilled in the art. However, the bulk specific gravity (Gsb) of a sample 300 of soil or aggregate, or the maximum specific gravity (Gmm) of a sample 300 of bituminous paving material, may also be determined. More particularly, the Gsb and Gmm parameters are skewed from the absolute or apparent specific gravity Gsa due to absorption of the gas by the sample 300. Thus, according to one advantageous aspect of the present invention, the pressure changes in the second vessel 200 ($V_2$) as the gas is expanded into the first vessel 100 ($V_1$) may be monitored as the gas absorbed by the sample 300 bleeds therefrom upon opening the valve mechanism 400 between the vessels 100, 200. As a result, the envelope volume (as opposed to the absolute volume upon equilibration of the pressures in the vessels 100, 200), and thus the envelope density, of the sample 300 may be determined, as described further below. The envelope density of the sample 300 is, in the case of soils and aggregates, the bulk specific gravity (Gsb), while, in the case of a bituminous paving material, the envelope density is the maximum specific gravity (Gmm). That is, the envelope density of the sample 300 is determined as the volume defined essentially by the outer surfaces of the sample 300 and includes any porosity within the sample 300. The difference between the absolute (apparent) and bulk or maximum specific gravities are thus related to the absorption of the sample 300, and may also provide an indication of the permeability characteristics thereof.

Figure 2:
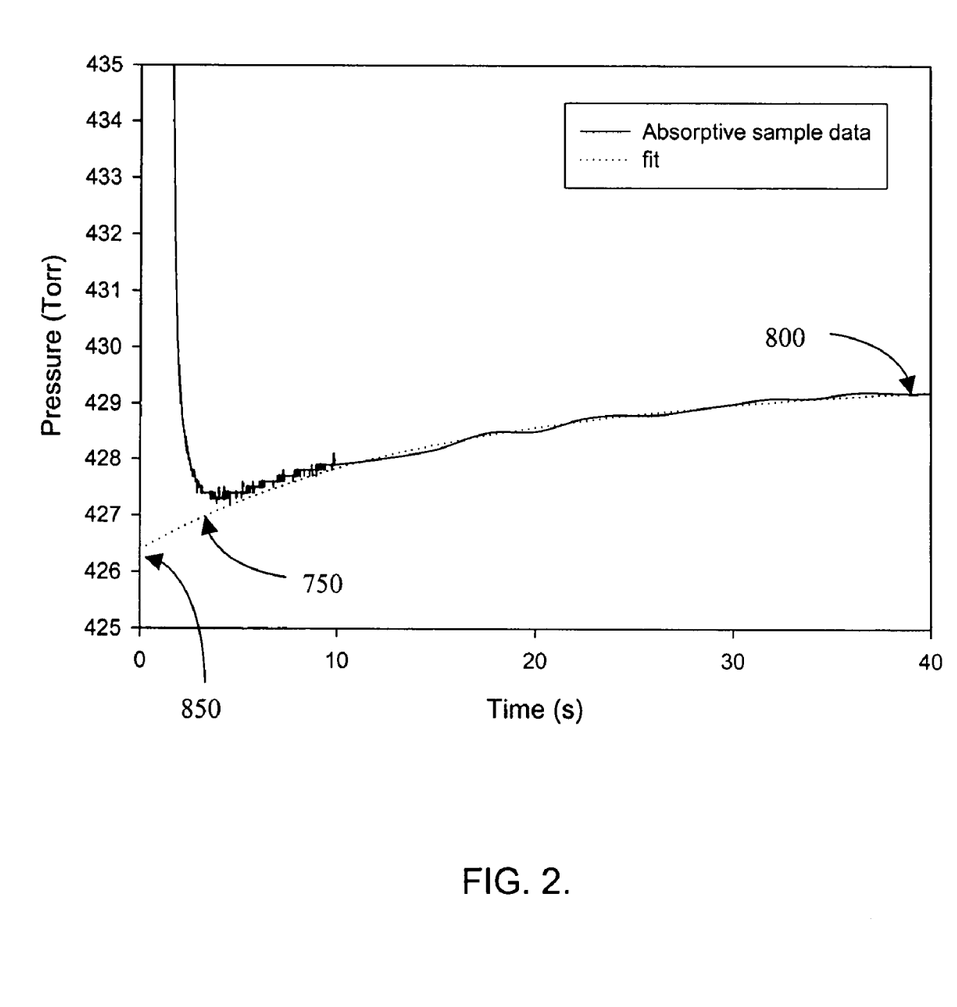
FIG. 2 is a schematic graph illustrating the pressure vs. time in the second vessel containing the sample as the valve mechanism is opened in order to equilibrate the pressure between then first and second vessels according to one embodiment of the present invention.

More particularly, when the valve mechanism 400 is initially opened to equilibrate the pressure between the two vessels 100, 200, it has been found that the pressure in the second vessel 200 (containing the sample 300), as experienced by the monitoring device 700 and as shown in FIG. 2, decays with a functional form equivalent to four coupled over-damped harmonic oscillators. At the same time, the gas absorbed in the sample 300 begins to diffuse or bleed from the sample 300, which causes the pressure to rise to the equalization pressure 800 ($P_s$), the pressure rise having the functional form:

$$y = y_0 + a \cdot (1 - e^{-b \cdot x}) + c \cdot (1 - e^{-d \cdot x})$$

As further shown in FIG. 2, the data between the minimum or base pressure 750 and the equalization pressure 800, for example, the data between the first damped out harmonic oscillator and the equalization pressure 800, may be used to extrapolate the trend of the data back to time t=0. Such an extrapolation back to time t=0 provides an indication of the theoretical minimum pressure 850 attained by the system 10 under a presumption that such a theoretical minimum pressure 850 would be attained if the valve mechanism 400 instantaneously opened and/or the system 10 allowed the vessels 100, 200 to be immediately connected before any of the gas could diffuse from the sample 300. Thus, the extrapolated theoretical minimum pressure 850 allows the envelope volume to be determined, the envelope volume of the sample 300 comprising the absolute volume of the sample 300 plus the volume of the pores therein. The envelope volume may thereafter be used to determine, for example, the theoretical maximum specific gravity (Gmm) of a sample 300 of bituminous paving material, or the bulk specific gravity (Gsb) of a sample 300 of soil or aggregate, having that envelope volume. Accordingly, the absolute volume, which is determined from the final equalization pressure 800, and the envelope volume, which is determined from the extrapolated theoretical minimum pressure 850, can be used to determine the volume of the pores within the sample 300 and, in turn, the absorption characteristics of the sample 300. Further, the absorption characteristics of the sample 300 may be entered into a function describing the relationship between gas absorption and water absorption so as to determine the water absorption for the sample 300.

Figure 3:
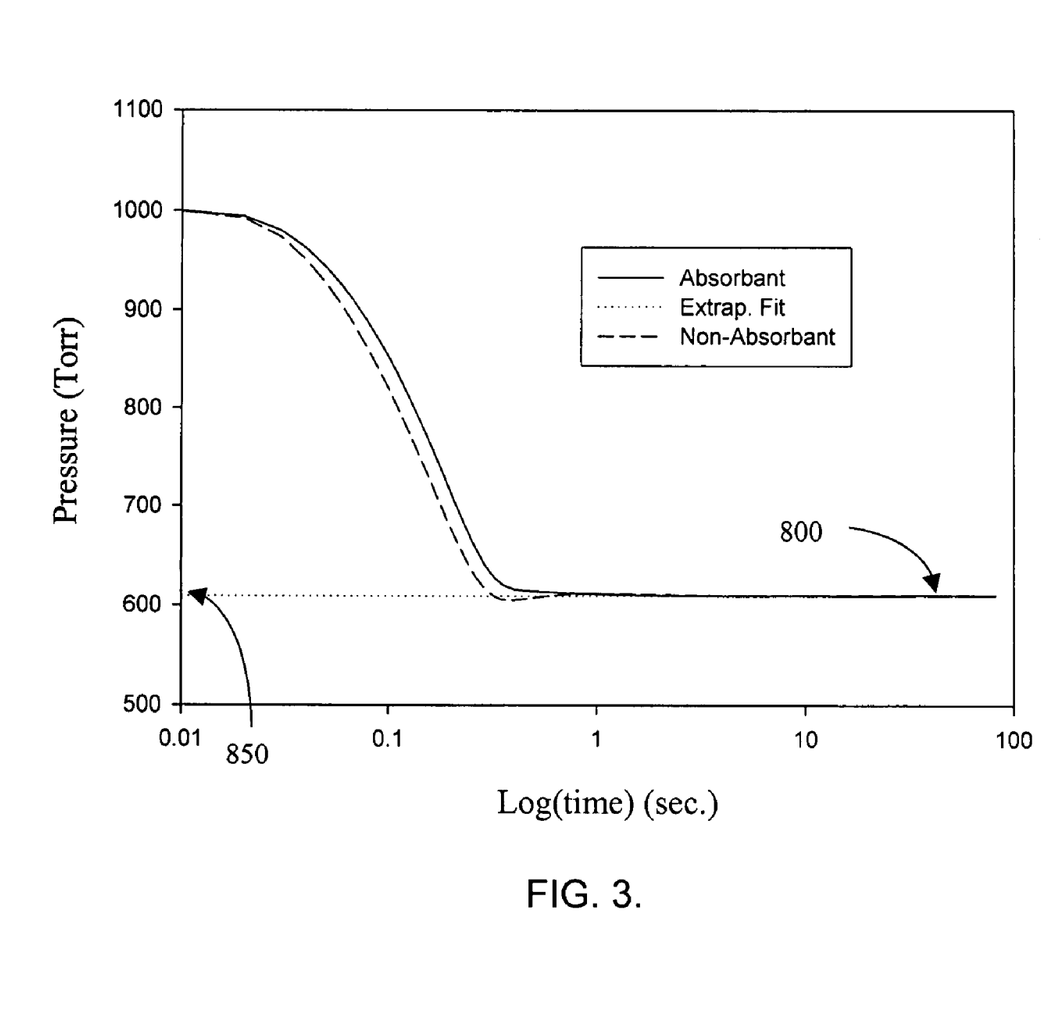
FIG. 3 is a schematic graph illustrating the pressure vs. log (time) in the second vessel for the sample and a substantially nonabsorbent specimen, respectively, as the valve mechanism is opened in order to equilibrate the pressure between then first and second vessels according to one embodiment of the present invention.

In some instances, the envelope volume determined from the theoretical minimum pressure 850 is more accurate when the pores in the sample 300 are small. That is, for a sample 300 having small volume pores, the diffusion of the gas from the pores is relatively slow, and thus the theoretical minimum pressure 850 is sufficiently accurate for determining the envelope volume of the sample 300. However, in instances where the sample 300 also includes larger pores (exhibits greater absorption), the diffusion of the gas from these larger pores may be relatively fast and therefore the envelope volume of such a sample 300 may not be accurately modeled by the theoretical minimum pressure 850 alone. Such a sample 300 may be identified, for example, from a comparison of a pressure vs. log (time) curve for that sample 300 as compared to a pressure vs. log (time) curve for a substantially nonabsorbent specimen having about the same envelope volume as the sample 300, as shown in FIG. 3. A substantially nonabsorbent specimen may be comprised of, for instance, aluminum or the like, and will exhibit, for example, a faster pressure drop upon opening the valve mechanism 400 and a higher rate of equilibration to the final equalization pressure 800 than a sample 300 exhibiting absorbency (porosity). Thus, such a comparison between pressure vs. time curves for the sample 300 and the substantially nonabsorbent specimen, respectively, may be manually performed by an operator or, for example, by an appropriate computer device, and may also provide an indication of the relative absorbency of the sample 300.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of nondestructively determining a property of a porous sample having a mass, said method comprising:

evacuating a first vessel to a sub-atmospheric pressure;

establishing a test pressure in a second vessel having the sample disposed therein, the test pressure being greater than the sub-atmospheric pressure;

equalizing the pressures of the first and second vessels by opening a valve mechanism operably engaged between the first and second vessels, each of the first and second vessels thereby experiencing a pressure change, the pressure change in the second vessel exhibiting an initial pressure drop followed by a transition to an equalization pressure on a pressure vs. time curve;

determining an envelope volume of the sample from a minimum pressure attained by the second vessel upon initial opening of the valve mechanism, the minimum pressure being related to the initial pressure drop; and determining an envelope density of the sample as a quotient of the mass and the envelope volume of the sample.

2. A method according to claim 1 further comprising determining an absolute volume of the sample from the equalization pressure of the second vessel.

3. A method according to claim 2 further comprising determining an absolute density of the sample as a quotient of the mass and the absolute volume of the sample.

4. A method according to claim 3 wherein the sample comprises an asphalt paving mix and the method further comprises determining a theoretical maximum specific gravity (Gmm) of the asphalt paving mix sample us a quotient of the absolute density of the sample and a density of water at about 25° C.

5. A method according to claim 1 wherein the sample is selected from the group consisting of a soil sample and an aggregate sample and the method further comprises determining a bulk specific gravity (Gsb) of the sample as a quotient of the envelope density of the sample and a density of water at about 25° C.

6. A method according to claim 3 wherein the sample is selected from the group consisting of a soil sample and an aggregate sample and the method further comprises determining an absolute specific gravity (Gsa) of the sample as a quotient of the absolute density of the sample and a density of water at about 25° C.

7. A method according to claim 1 further comprising purging tile first and second vessels using at least one purge cycle, each purge cycle comprising evacuating the first and second vessels and then filling the first and second vessels with a substantially inert gas.

8. A method according to claim 1 wherein evacuating the first vessel further comprises evacuating die first vessel to a pressure of about 20 Torr.

9. A method according to claim 1 wherein establishing the test pressure in the second vessel further comprises establishing a pressure of about 700 Torr in the second vessel.

10. A method according to claim 1 wherein determining the envelope volume of the sample further comprises determining the envelope volume of the sample from the minimum pressure, the minimum pressure being determined according to an analysis comprising modeling the transition between the initial pressure drop and the equalization pressure on the pressure vs. time curve so as to produce a beat-fit equation and then determining, using the equation, the minimum pressure attained by the second vessel upon initial opening of the valve mechanism.

11. A method according to claim 1 further comprising:
determining the envelope volume of the sample from the minimum pressure, the minimum pressure being determined according to an analysis comprising modeling the transition between the initial pressure drop and the equalization pressure on the pressure vs. time curve so as to produce a best-fit equation and then determining, using the equation, the minimum pressure attained by the second vessel upon initial opening of the valve mechanism;

determining a pressure vs. time curve for a substantially nonabsorbent specimen having an envelope volume substantially the same as the sample envelope volume by substituting the substantially nonabsorbent specimen for the sample in the second vessel and ten equalizing the pressures between the first and second vessels; and comparing the pressure vs. time curves for the substantially nonabsorbent specimen to the pressure vs. time curve for the sample so as to determine the relative absorption of the sample.

12. A system for nondestructively determining a property of a porous sample having a mass, said system comprising:

a first vessel capable of being evacuated to a sub-atmospheric pressure;

a second vessel having the sample disposed therein and capable of being established at a test pressure, the test pressure being greater than the sub-atmospheric pressure;

a valve mechanism operably engaged between the first and second vessels and configured such that opening or the valve mechanism allows the pressures of the first and second vessels to equalize to an equalization pressure; and a monitoring device configured to determine a pressure change in the second vessel when the valve mechanism is opened, the pressure change being indicative of a minimum pressure attained by the second vessel upon initial opening of the valve mechanism, the minimum pressure being related to an envelope volume, a quotient of the mass and the envelope volume of the sample thereby providing an envelope density of the sample.

13. A system according to claim 12 wherein the monitoring device is further configured to determine an absolute volume of the sample from the equalization pressure of the second vessel, a quotient of the mass and the absolute volume of the sample thereby providing an absolute density of the sample.

14. A system according to claim 12 further comprising a purging mechanism configured to purge the first and second vessels using at least one purge cycle, each purge cycle comprising evacuating the first and second vessels and then filling the first and second vessels with a substantially inert gas.

15. A system according to claim 14 wherein the purging mechanism is further configured to evacuate the first vessel to a pressure of about 20 Torr.

16. A system according to claim 14 wherein the purging mechanism is further configured to establish the test pressure of about 700 Torr in the second vessel.

17. A system according to claim 12 wherein the first vessel and the second vessel define a volume ratio of about 2:5.

18. A system according to claim 12 wherein at least the first vessel is comprised of aluminum.

19. A system according to claim 12 further comprising a computer device operably engaged with at least one of the second vessel and the monitoring device and configured to model the transition between the initial pressure drop and the equalization pressure on the pressure vs. time curve so as to produce a best-fit equation, determine, using the equation, the minimum pressure attained by the second vessel upon initial opening of the valve mechanism, and determine the envelope volume of the sample from the minimum pressure.

20. A system according to claim 12 further comprising a computer device operably engaged with at least one of the second vessel and the monitoring device and configured to:

model the transition between the initial pressure drop and the equalization pressure on the pressure vs. time curve so as to produce a best-fit equation, determine, using the equation, the minimum pressure attained by the second vessel upon initial opening of the valve mechanism, and determine the envelope volume of the sample from the minimum pressure;

determine a pressure vs. time curve for a substantially nonabsorbent specimen having an envelope volume substantially the same as the sample envelope volume, substituted for the sample in the second vessel, upon equalization of the pressures between the first and second vessels; and     compare the pressure vs. time curves for the substantially nonabsorbent specimen to the pressure vs. time curve for the sample so as to determine the relative absorption of the sample.

\* \* \* \* \*

UNITED STATES PATENT AND TRADEMARK OFFICE
CERTIFICATE OF CORRECTION

PATENT NO. : 6,990,848 B2
DATED : January 31, 2006
INVENTOR(S) : Dummer et al.

It is certified that error appears in the above-identified patent and that said Letters Patent is hereby corrected as shown below:

Column 9,
Line 28, "sample us a" should read -- sample as a --;
Line 44, "purging tile" should read -- purging the --;
Line 49, "die first" should read -- the first --;
Line 61, "beat-fit" should read -- best-fit --.

Column 10,
Line 12, "ten" should read -- then --;
Line 29, "opening or" should read -- opening of --.

Signed and Sealed this

Fourth Day of April, 2006

JON W. DUDAS
*Director of the United States Patent and Trademark Office*